United States Patent
Michelmore

(10) Patent No.: US 10,487,336 B2
(45) Date of Patent: Nov. 26, 2019

(54) METHODS FOR SELECTING PLANTS AFTER GENOME EDITING

(71) Applicant: The Regents of the University of California, Oakland, CA (US)

(72) Inventor: Richard Michelmore, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 74 days.

(21) Appl. No.: 15/303,707

(22) PCT Filed: May 7, 2015

(86) PCT No.: PCT/US2015/029690
§ 371 (c)(1),
(2) Date: Oct. 12, 2016

(87) PCT Pub. No.: WO2015/171894
PCT Pub. Date: Nov. 12, 2015

(65) Prior Publication Data
US 2017/0029831 A1 Feb. 2, 2017

Related U.S. Application Data

(60) Provisional application No. 61/991,173, filed on May 9, 2014.

(51) Int. Cl.
*C12N 15/82* (2006.01)

(52) U.S. Cl.
CPC ................. *C12N 15/8213* (2013.01)

(58) Field of Classification Search
None
See application file for complete search history.

(56) References Cited

U.S. PATENT DOCUMENTS

| | | | |
|---|---|---|---|
| 2006/0253934 A1 | 11/2006 | Yadav | |
| 2009/0136646 A1 | 5/2009 | Gingera et al. | |
| 2012/0054896 A1* | 3/2012 | Long | A01H 1/04 800/263 |
| 2015/0291967 A1* | 10/2015 | Mathis | C12N 15/8209 800/300.1 |
| 2016/0312233 A1* | 10/2016 | Duchateau | C12N 15/79 |

OTHER PUBLICATIONS

Feng et al. Multigeneration analysis reveals the inheritance, specificity, and patterns of CRISPR/Cas-induced gene modifications in *Arabidopsis*. Proc Natl Acad Sci U S A. Mar. 25, 2014;111(12):4632-7. Epub Feb. 18, 2014.*

Huo et al. Expression of 9-cis-Epdxycarotenoid Dioxygenase4 is essential for thermoinhibition of lettuce seed germination but not for seed development or stress tolerance. Plant Cell. Mar. 2013;25(3):884-900. Epub Mar. 15, 2013. (Year: 2013).*

Tamura et al. Isolation and characterization of high temperature-resistant germination mutants of *Arabidopsis thaliana*. Plant Cell Physiol. Aug. 2006;47(8):1081-94. Epub Jul. 2, 2006. (Year: 2006).*

Smith et al. Transformation of plants via the shoot apex. Methods Mol Biol. 1990;6:335-40. (Year: 1990).*

Clough. Floral dip: agrobacterium-mediated germ line transformation. Methods Mol Biol. 2005;286:91-102. (Year: 2005).*

Galbiati et al. Large-scale T-DNA mutagenesis in *Arabidopsis* for functional genomic analysis. Funct Integr Genomics. May 2000;1(1):25-34. (Year: 2000).*

Hendel et al. Quantifying on- and off-target genome editing. Trends Biotechnol. Feb. 2015;33(2):132-40. Epub Jan. 13, 2015. Review. (Year: 2015).*

International Search Report from PCT/US15/29690, dated Aug. 5, 2015, 4 pages.

Feng et al., "Multigeneration Analysis Reveals the Inheritance, Specificity, and Patterns of CRISPR/Cas-induced Gene Modifications in *Arabidopsis*," PNAS, vol. 111, No. 12, Mar. 25, 2014, pp. 4632-4637.

Forner et al., "Germline-Transmitted Genome Editing in *Arabidopsis thaliana* Using TAL-Effector-Nucleases," PLOS ONE, vol. 10(3), Mar. 20, 2015, 15 pages.

Gao et al., "Specific ad Heritable Gene Editing in *Arabidopsis*," PNAS, vol. 111, No. 12, Mar. 25, 2014, pp. 4357-4358.

Papi et al., "Identification and Disruption of an *Arabidopsis* Zinc Finger Gene Controlling Seed Germination," Genes & Development, 2000, vol. 14, No. 1, pp. 28-33.

Zhong et al., "The Competence of Maize Shoot Meristems for Integrative Transformation and Inherited Expression of Transgenes," Plant Physiol., (1996), 110: pp. 1097-1107.

* cited by examiner

*Primary Examiner* — Cynthia E Collins

(74) *Attorney, Agent, or Firm* — Kilpatrick Townsend and Stockton LLP

(57) ABSTRACT

The disclosure provides methods for selecting modified plants with a mutation in a target gene and plants produced by the methods. Specifically, the disclosure provides methods comprising introducing a recombinant expression cassette encoding a genome editing protein into meristematic or germline cells of a parent plant, wherein the genome editing protein specifically recognizes a target gene; crossing or selfing the parent plant, thereby producing a plurality of progeny seeds; and selecting progeny plants grown from the progeny seeds that express a phenotype that can be selected at the intact plant level.

17 Claims, No Drawings

METHODS FOR SELECTING PLANTS AFTER GENOME EDITING

CROSS-REFERENCE TO RELATED APPLICATIONs

This application is a U.S. National Phase Application of PCT/US2015/029690, International Filing Date May 7, 2015 which claims benefit under 35 U.S.C.§ 119(e) to US Application No. 61/991,173, filed May 9, 2014, the contents of which are incorporated herein by reference.

FIELD OF THE INVENTION

The present invention relates to methods of conferring a desired phenotype on a plant by specifically mutating a target gene in a plant using a genome editing procedure.

BACKGROUND OF THE INVENTION

Recent advances in gene editing technologies have provided opportunities for precise modification of the genome in many types of organisms, including plants and animals. In particular, technologies based on genome editing proteins, such as zinc finger nucleases, TALENs, and CRISPR-Cas9 systems are advancing rapidly and it is now possible to target genetic changes to specific DNA sequences in the genome (see e.g., Segal, et at. (2013) *Annu. Rev. Genomics Hum. Genet.* 14, 135-158; Sander, et at. (2014) *Nature Biotech.* 32, 347-355). These can be either mutations resulting in gene knockouts or substitutions of one allele for another. Highly efficient CRISPR-mediated precise genome modification has now been demonstrated in several plants. In most plants, it is necessary to go through tissue culture to obtain modifications of the germline. Tissue culture can be mutagenic and therefore there is the likelihood of introducing unpredictable and undesired background, off-target mutations in addition to the desired changes. Also, it remains challenging to select for cells with the targeted genome modification.

What is desired is a method that does not require going through tissue culture and allows the selection of modified cells without the use of selectable transgenes. The present invention provides these and other advantages.

BRIEF SUMMARY OF THE INVENTION

This invention provides method for selecting modified plants with a mutation in a target gene and plants produced by the methods. The methods comprise (a) introducing a first recombinant expression cassette encoding a first genome editing protein or protein plus oligonucleotide (e.g., a guide RNA) into meristematic or germline cells of a parent plant, wherein the first genome editing protein or protein plus oligonucleotide (e.g., a guide RNA) specifically recognizes the target gene; (b) introducing a second recombinant expression cassette encoding a second genome editing protein or protein plus oligonucleotide (e.g., a guide RNA) into meristematic or germline cells of the parent plant, wherein the second genome editing protein or protein plus oligonucleotide specifically recognizes a gene controlling seed germination; (c) after steps (a) and (b), crossing or selfing the parent plant, thereby producing a plurality of progeny seed (e.g., first generation progeny); (d) selecting progeny plants grown from the progeny seed that express a phenotype that can be selected at the intact plant level. In some embodiments, this phenotype is the ability to germinate under conditions that inhibit germination of seed which lack a mutation in the gene controlling seed germination; and (e) identifying the progeny plants selected in step (d) that comprise a mutation in the target gene, thereby selecting modified plants with a mutation in the target gene The recombinant expression cassettes can be introduced into the cells in vitro or in planta. The method of the invention can be used with essentially any plant. In some embodiments, the parent plant is lettuce. The gene controlling seed germination can be one that inhibits germination at high temperatures (e.g., at or above 30° C.). An exemplary gene for this purpose is LsNCED4 in lettuce.

A number of genome editing proteins can be used in the invention. Examples include, zinc finger nucleases, TALENs, or Cas-9 nucleases guided by a guide RNA (gRNA). The genome editing proteins can be used to introduce a single strand nick or a double strand break in the target gene, which is repaired and leads to a mutation in the target sequence. The genome editing proteins can also be used to introduce a desired nucleotide sequence into the target gene by homologous recombination.

The expression cassettes can be introduced into the cells using techniques, including use of *Agrobacterium*, particle bombardment, or microinjection. The expression cassettes can be integrated into the genome of the plant or the genome editing proteins can be transiently expressed in the cells.

The methods of the invention can be used to confer any desired phenotype on the plants. Exemplary phenotypes include resistance to plant pathogens, resistance to stress conditions (biotic or abiotic), increased yield, or changes plant development.

DEFINITIONS

The term "plant" includes whole plants, shoot vegetative organs/structures (e.g., leaves, stems and tubers), roots, flowers and floral organs/structures (e.g., bracts, sepals, petals, stamens, carpels, anthers and ovules), seed (including embryo, endosperm, and seed coat) and fruit (the mature ovary), plant tissue (e.g., vascular tissue, ground tissue, and the like) and cells (e.g., guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

The term "progeny" refers generally to the offspring of selfing or a cross and includes direct first generation progeny (e.g., F1), as well as later generations (e.g., F2, F3, etc).

As used herein, "transgenic plant" includes reference to a plant that comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid, including those transgenics initially so altered as well as those created by sexual crosses or asexual propagation from the initial transgenic.

A "non-transgenic plant" is a plant that lacks a heterologous polynucleotide stably integrated into its genome. Such a plant may comprise alterations of its genome (chromosomal or extra-chromosomal) that are introduced by the methods of the invention, conventional plant breeding methods or by naturally occurring events such as random cross-fertilization, non-recombinant viral infection, non-recombinant bacterial transformation, non-recombinant transposition, or spontaneous mutation.

The term "expression cassette" refers to any recombinant expression system for the purpose of expressing a nucleic acid sequence of the invention in vitro or in vivo, constitutively or inducibly, in any cell, including, in addition to plant cells, prokaryotic, yeast, fungal, insect or mammalian cells. The term includes linear and circular expression systems. The term includes all vectors. The cassettes can remain episomal or integrate into the host cell genome. The expression cassettes can have the ability to self-replicate or not (i.e., drive only transient expression in a cell). The term includes recombinant expression cassettes that contain only the minimum elements needed for transcription of the recombinant nucleic acid.

The term "constitutive" or "constitutively" denotes temporal and spatial expression of the polypeptides of the present invention in plants in the methods according to various exemplary embodiments of the invention. The term "constitutive" or "constitutively" means the expression of the polypeptides of the present invention in the tissues of the plant throughout the life of the plant and in particular during its entire vegetative cycle. In some embodiments, the polypeptides of the present invention are expressed constitutively in all plant tissues. In some embodiments, the polypeptides of the present invention are expressed constitutively in the roots, the leaves, the stems, the flowers, and/or the fruits. In other embodiments of the invention, the polypeptides of the present invention are expressed constitutively in the roots, the leaves, and/or the stems.

The term "inducible" or "inducibly" means the polypeptides of the present invention are not expressed, or are expressed at very low levels, in the absence of an inducing agent. The expression of the polypeptides of the present invention is greatly induced in response to an inducing agent.

The term "inducing agent" is used to refer to a chemical, biological or physical agent or environmental condition that effects transcription from an inducible regulatory element. In response to exposure to an inducing agent, transcription from the inducible regulatory element generally is initiated de novo or is increased above a basal or constitutive level of expression. Such induction can be identified using the methods disclosed herein, including detecting an increased level of RNA transcribed from a nucleotide sequence operatively linked to the regulatory element, increased expression of a polypeptide encoded by the nucleotide sequence, or a phenotype conferred by expression of the encoded polypeptide.

The phrase "substantially identical," in the context of the present invention refers to polynucleotides or polypeptides that have sufficient sequence identity with a reference sequence to effect similar functionality when expressed in plants as the reference sequence. In accordance with one aspect of an exemplary embodiment of the invention, a polynucleotide or a polypeptide that exhibits at least 90% sequence identity with a reference sequence may be deemed to be "substantially identical;" however, polynucleotides and polypeptides that exhibit less (even significantly less, e.g., 60%-70% or less) than 90% sequence identity may, in accordance with various exemplary embodiments of the invention, be "substantially identical" to their reference sequences if requisite functionality is achieved. Alternatively, percent identity can be any value from 90% to 100%. More preferred embodiments include at least: 90%, 95%, or 99% identity as used herein is as compared to the reference sequence using the programs described herein; preferably BLAST using standard parameters, as described below.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions, such as from 20 to 600, usually about 50 to about 200, more usually about 100 to about 150, in which a sequence may be compared to a reference sequence of the same number of contiguous positions after the two sequences are optimally aligned. If no range is provided, the comparison window is the entire length of the reference sequence. Methods of alignment of sequences for comparison are well-known in the art. Optimal alignment of sequences for comparison can be conducted e.g., by the local homology algorithm of Smith and Waterman, *Adv. Appl. Math.* 2:482, 1981; by the homology alignment algorithm of Needleman and Wunsch, *J. Mol. Biol.* 48:443, 1970; by the search for similarity method of Pearson and Lipman, *Proc. Nat'l. Acad. Sci. USA* 85:2444, 1988; by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

An example of an algorithm that is suitable for determining percent sequence identity and sequence similarity is the BLAST algorithm, which is described in Altschul, S. F. et al., *J. Mol. Biol.* 215:403-410, 1990. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul, S. F. et al., supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff and Henikoff, *Proc. Natl. Acad. Sci. USA* 89:10915, 1989), alignments (B) of 50, expectation (E) of 10, M=5, N=−4, and a comparison of both strands.

The BLAST algorithm also performs a statistical analysis of the similarity between two sequences (see, e.g., Karlin and Altschul, *Proc. Nat'l. Acad. Sci. USA* 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, preferably less than about 0.01, and more preferably less than about 0.001.

DETAILED DESCRIPTION

The present invention provides methods of conferring a desired phenotype on plants by specifically mutating a target gene in the plant using a first genome editing protein to mutate the target gene and a second genome editing protein to mutate a second gene controlling a phenotype that can be selected at the whole plant level (e.g., a gene that controls seed germination). Plants are selected based on the presence of a mutation in the second gene (e.g., by the ability of seed to germinate under conditions that inhibit germination of wild type plants) and secondarily on the presence of a mutation in the target gene.

The methods of the invention take advantage of the high rates of simultaneous genetic changes that occur with genome editing proteins CRISPR-Cas9 technology and the ability to specifically modify traits that are controlled by a single gene and that can be selected at the whole plant level after modification. An example of such a trait is temperature sensitivity of seed germination being determined by a single gene. It is known that genome editing proteins introduce gene modifications at high frequency multiple times within the same cell. In some systems up to 30% of the cells contain homozygous changes, i.e. both alleles have been modified. If multiple genes are targeted simultaneously, up to 10% of cells have modifications in multiple genes and up to five genes have been modified simultaneously.

Generally, genome editing proteins or proteins plus oligonucleotide of the invention result in targeted cleavage of genomic DNA (e.g., a single strand nick or a double strand break). All eukaryotic organisms, including plants, repair breaks in DNA using highly conserved DNA repair mechanisms such as the non-homologous end joining or the homology-directed repair pathways that can lead to sequence modifications at the site of break. The non-homologous end joining repair pathway, for example, ligates the two broken ends, but can introduce small insertions and/or deletions at the site of the break, which can disrupt a target gene. In some embodiments two double strand breaks are made, repairing the double strand results in removing the material between the double strand breaks and rejoining the ends of the nucleotide sequence so as to excise the sequences between the double strand breaks. Alternatively, a homologous donor DNA, that contains homologous overlaps with DNA on either side of the double strand break, can be provided in combination with the genome editing protein. Homologous recombination at the site of the break results in the replacement of a target sequence by the donor DNA sequence.

One of skill will recognize that the ability to engineer a trait relies on the action of the genome editing proteins and various endogenous DNA repair pathways. These pathways may be normally present in a cell or may be induced by the action of the genome editing protein. Using genetic and chemical tools to over-express or suppress one or more genes or elements of these pathways can improve the efficiency and/or outcome of the methods of the invention. For example, it can be useful to over-express certain homologous recombination pathway genes or suppression of non-homologous pathway genes, depending upon the desired modification.

It may also desirable to increase the odds of recovering a properly targeted event rather than a randomly integrated event. Steps may include, but are not limited to, the use of a positive-negative selection system to reduce the recovery of non-targeted events (Terada et at. 2004 *Plant Cell Reports*, 22:653-9).

The methods of the invention can be used to confer a desired phenotype on essentially any plant. The invention thus has use over a broad range of agronomically important species including species from the genera *Asparagus, Atropa, Aven, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Nicotiana, Oryza, Panieum, Pannesetum, Persea, Pisum, Pyrus, Prunus, Raphanus, Secale, Senecio, Sinapis, Solanum, Sorghum, Trigonella, Triticum, Vitis, Vigna,* and *Zea*. In the case of selection for germination at high temperature, many although not all, species are sensitive to thermoinhibition of germination, examples of crop species that will not normally germinate at temperature include but are not limited to lettuce, spinach, carrots, and celery.

Genome Editing Proteins

Any of a number of genome editing proteins well known to those of skill in the art can be used in the methods of the invention. The particular genome editing protein used is not critical, so long as it provides site specific mutation of a desired nucleic acid sequence. Exemplary genome editing proteins include targeted nucleases such as engineered zinc finger nucleases (ZFNs), transcription-activator like effector nucleases (TALENs), and engineered meganucleases. In addition, the CRISPR/Cas system with an engineered RNA (e.g., a gRNA) to guide the nuclease (e.g., Cas-9) to the target cleavage site can be used.

Zinc Finger Nucleases

Zinc finger nucleases (ZFNs) are engineered proteins comprising a zinc finger DNA-binding domain fused to a nucleic acid cleavage domain, e.g., a nuclease. The zinc finger binding domains provide specificity and can be engineered to specifically recognize any desired target DNA sequence. For a review of the construction and use of ZFNs in plants and other organisms, see Urnov et at. 2010 *Nat Rev Genet.* 11(9):636-46.

The zinc finger DNA binding domains are derived from the DNA-binding domain of a large class of eukaryotic transcription factors called zinc finger proteins (ZFPs). The DNA-binding domain of ZFPs typically contains a tandem array of at least three fingers each recognizing a specific triplet of DNA. ZFPs have been identified in plants, where they are involved in, for example, developmental regulation of various floral and vegetative organs. In plant ZFPs, zinc fingers do not generally occur in closely-spaced tandem arrays but may be separated by an intervening stretch of up to 200 amino acids. The binding capability of this class of ZFPs appears to be determined by both the zinc fingers and the intervening amino acids, suggesting that plant ZFPs have a different mechanism of DNA binding as compared to ZFPs derived from other organisms.

One of skill will recognize that a number of strategies can be used to design the binding specificity of the zinc finger binding domain. One approach, termed "modular assembly," relies on the functional autonomy of individual fingers with DNA. In this approach, a given sequence is targeted by identifying zinc fingers for each component triplet in the sequence and linking them into a multifinger peptide. Several alternative strategies for designing zinc finger DNA binding domains have also been developed. These methods are designed to accommodate the ability of zinc fingers to contact neighboring fingers as well as nucleotides bases outside their target triplet.

Typically, the engineered zinc finger DNA binding domain has a novel binding specificity, compared to a naturally-occurring zinc finger protein. Engineering methods include, for example, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See e.g., U.S. Pat. Nos. 6,453,242 and 6,534,261. Exemplary selection methods, including phage display and two-hybrid systems, are well known and described in the literature. In addition, enhancement of binding specificity for zinc finger binding domains has been described in WO 02/077227.

In addition, individual zinc finger domains may be linked together using any suitable linker sequences. See, U.S. Pat. Nos. 6,479,626; 6,903,185; and 7,153,949 for exemplary linker sequences. The ZFNs of the invention may include any combination of suitable linkers between the individual zinc fingers of the protein.

The nucleic acid cleavage domain is non-specific and is typically a restriction endonuclease, such as FokI. This endonuclease must dimerize to cleave DNA. Thus, cleavage by FokI as part of a ZFN requires two adjacent and independent binding events, which must occur in both the correct orientation and with appropriate spacing to permit dimer formation. The requirement for two DNA binding events enables more specific targeting of long and potentially unique recognition sites. FokI variants with enhanced activities have been described. See e.g., Guo, et at. 2010 *J. Mol. Biol.* 400:96-107.

Transcription-Activator Like Effector Nucleases (TAL-ENs)

Transcription activator like effectors (TALEs) are proteins secreted by certain species of *Xanthomonas* to modulate gene expression in host plants and to facilitate bacterial colonization and survival. TALEs act as transcription factors and modulate expression of resistance genes in the plants. Recent studies of TALEs have revealed the code linking the repetitive region of TALEs with their target DNA-binding sites. TALEs comprise a highly conserved and repetitive region consisting of tandem repeats of mostly 33 or 34 amino acid segments. The repeat monomers differ from each other mainly at amino acid positions 12 and 13. A strong correlation between unique pairs of amino acids at positions 12 and 13 and the corresponding nucleotide in the TALE-binding site have been found. The simple relationship between amino acid sequence and DNA recognition of the TALE binding domain allows for the design DNA binding domains of any desired specificity.

TALEs can be linked to a non-specific DNA cleavage domain to prepare genome editing proteins, referred to as TALENs. As in the case of ZFNs, a restriction endonuclease, such as FokI, can be conveniently used. For a description of the use of TALENs in plants, see Mahfouz et at. 2011 *Proc Natl Acad Sci USA*. 108:2623-8 and Mahfouz 2011 *GM Crops*. 2:99-103.

Meganucleases

Meganucleases are endonucleases that have a recognition site of 12 to 40 base pairs. As a result, the recognition site occurs rarely in any given genome. By modifying the recognition sequence through protein engineering, the targeted sequence can be changed and the nuclease can be used to cleave a desired target sequence. (See Seligman, et at. 2002 *Nucleic Acids Research* 30: 3870-9 WO06097853, WO06097784, WO04067736, or US20070117128).

CRISPR/Cas System

CRISPR (Clustered Regularly Interspaced Short Palindromic Repeats)/Cas (CRISPR-associated) system, are adaptive defense systems in prokaryotic organisms that cleave foreign DNA. CRISPR loci in microbial hosts contain a combination of CRISPR-associated (Cas) genes as well as non-coding RNA elements which determine the specificity of the CRISPR-mediated nucleic acid cleavage. Three types (I-III) of CRISPR systems have been identified across a wide range of bacterial hosts. In the typical system, a Cas endonuclease (e.g., Cas9) is guided to a desired site in the genome using small RNAs that target sequence-specific single- or double-stranded DNA sequences. The CRISPR/Cas system has been used to induce site specific mutations in plants (see Miao et at. 2013 *Cell Research* 23:1233-1236).

The basic CRISPR system uses two non-coding guide RNAs (crRNA and tracrRNA) which form a crRNA:tracrRNA complex that directs the nuclease to the target DNA via Wastson-Crick base-pairing between the crRNA and the target DNA. Thus, the guide RNAs can be modified to recognize any desired target DNA sequence. More recently, it has been shown that a Cas nuclease can be targeted to the target gene location with a chimeric single-guide RNA (sgRNA) that contains both the crRNA and tracRNA elements. It has been shown that Cas9 can be targeted to desired gene locations in a variety of organisms with a chimeric sgRNA (Cong et at. 2013 *Science* 339:819-23).

Introduction of Genome Editing Proteins into Plant Cells

The genome editing protein may be introduced into the plant cell using standard genetic engineering techniques, well known to those of skill in the art. In the typical embodiment, recombinant expression cassettes comprising a polynucleotide encoding a genome editing protein of the invention can be prepared according to well-known techniques. In the case of CRISPR/Cas nuclease, the expression cassette may transcribe the guide RNA, as well.

Such plant expression cassettes typically contain the polynucleotide operably linked to a promoter (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal.

A number of promoters can be used in the practice of the invention. A plant promoter fragment can be employed which will direct expression of the desired polynucleotide in all tissues of a plant. Such promoters are referred to herein as "constitutive" promoters and are active under most environmental conditions and state of development or cell differentiation. Examples of constitutive promoters include the cauliflower mosaic virus (CaMV) 35S transcription initiation region.

Alternatively, the plant promoter can direct expression of the polynucleotide under environmental control. Such promoters are referred to here as "inducible" promoters. Environmental conditions that may affect transcription by inducible promoters include biotic stress, abiotic stress, saline stress, drought stress, pathogen attack, anaerobic conditions, cold stress, heat stress, hypoxia stress, or the presence of light.

In addition, chemically inducible promoters can be used. Examples include those that are induced by benzyl sulfonamide, tetracycline, abscisic acid, dexamethasone, ethanol or cyclohexenol.

Examples of promoters under developmental control include promoters that initiate transcription only, or preferentially, in certain tissues such as leaves, roots, fruit, seeds, or flowers. These promoters are sometimes called tissue-preferred promoters. The operation of a promoter may also vary depending on its location in the genome. Thus, a developmentally regulated promoter may become fully or partially constitutive in certain locations. A developmentally regulated promoter can also be modified, if necessary, for weak expression.

Methods for transformation of plant cells are well known in the art, and the selection of the most appropriate transformation technique for a particular embodiment of the invention may be determined by the practitioner. Suitable methods may include electroporation of plant protoplasts, liposome-mediated transformation, polyethylene glycol (PEG) mediated transformation, transformation using viruses, micro-injection of plant cells, micro-projectile bombardment of plant cells, and *Agrobacterium tumeficiens* mediated transformation. Transformation means introducing a nucleotide sequence in a plant in a manner to cause stable or transient expression of the sequence.

In some embodiments of the invention, in planta transformation techniques (e.g., vacuum-infiltration, floral spraying or floral dip procedures) are used to introduce the expression cassettes of the invention (typically in an *Agrobacterium* vector) into meristematic or germline cells of a whole plant. Such methods provide a simple and reliable method of obtaining transformants at high efficiency while avoiding the use of tissue culture. (see, e.g., Bechtold et at. 1993 *C. R. Acad. Sci.* 316:1194-1199; Chung et at. 2000 *Transgenic Res.* 9:471-476; Clough et at. 1998 *Plant J.* 16:735-743; and Desfeux et at. 2000 *Plant Physiol* 123:895-904). In these embodiments, seed produced by the plant comprise the expression cassettes encoding the genome editing proteins of the invention. The seed can be selected based on the ability to germinate under conditions that inhibit germination of the untransformed seed.

If transformation techniques require use of tissue culture, transformed cells may be regenerated into plants in accordance with techniques well known to those of skill in the art. The regenerated plants may then be grown, and crossed with the same or different plant varieties using traditional breeding techniques to produce seed, which are then selected under the appropriate conditions.

The expression cassette can be integrated into the genome of the plant cells, in which case subsequent generations will express the genome editing proteins of the invention. Alternatively, the expression cassette is not integrated into the genome of the plants cell, in which case the genome editing proteins is transiently expressed in the transformed cells and is not expressed in subsequent generations.

In some embodiments, the genome editing protein itself, is introduced into the plant cell. In these embodiments, the introduced genome editing protein is provided in sufficient quantity to modify the cell but does not persist after a contemplated period of time has passed or after one or more cell divisions. In such embodiments, no further steps are needed to remove or segregate away the genome editing protein and the modified cell.

In these embodiments, the genome editing protein is prepared in vitro prior to introduction to a plant cell using well known recombinant expression systems (bacterial expression, in vitro translation, yeast cells, insect cells and the like). After expression, the protein is isolated, refolded if needed, purified and optionally treated to remove any purification tags, such as a His-tag. Once crude, partially purified, or more completely purified genome editing proteins are obtained, they may be introduced to a plant cell via electroporation, by bombardment with protein coated particles, by chemical transfection or by some other means of transport across a cell membrane.

The genome editing protein can also be expressed in *Agrobacterium* as a fusion protein, fused to an appropriate domain of a virulence protein that is translocated into plants (e.g., VirD2, VirE2, VirE2 and VirF). The Vir protein fused with the genome editing protein travels to the plant cell's nucleus, where the genome editing protein would produce the desired double stranded break in the genome of the cell. (see Vergunst et at. 2000 *Science* 290:979-82).

Selecting Plants with Desired Phenotypes

As noted above, one of the genome editing proteins plants of the invention induces mutations in a gene that confers a phenotype that can be selected at the whole plant level. Suitable genes that can be targeted for this purpose include genes that control seed germination (e.g., sensitivity to environmental conditions such as temperature, light, oxygen, water and the like), resistance to a pathogen, insensitivity to a chemical such as an herbicide or growth regulator, response to an environmental signal such as day length or temperature. Alternatively, the mutation may result in a visually detectable change in phenotype such as color or growth rate.

Plants typically have an upper or lower temperature limit at which seed germination will occur. This is under genetic control. For example, it is well documented in lettuce that inhibition of germination at high temperature is dependent on the activity of the LsNCED4 gene (see e.g., GenBank Accession JN788925.1). This gene encodes a regulated enzyme in the abscisic acid (ABA) biosynthetic pathway and if active the lettuce seed will not germinate at elevated temperatures (e.g., above 30° C.). If the gene is knocked out, the seed will germinate well at elevated temperatures. Therefore, the ability to germinate at high temperature provides a powerful screen for inactivation of the LsNCED4 gene. Of relevance to this invention, most, if not all, lettuce cultivars studied have an active LsNCED4 gene and therefore do not germinate at high temperature. Consequently, this gene provides a natural selectable marker for gene modification that is present in lettuce cultivars. Furthermore, inactivation of this gene seems to have no deleterious effect on the performance of the plant.

Thus, in a typical embodiment, the lettuce gene LsNCED4 can be used as a target of one of the genome editing proteins in the methods of the invention. The resultant seeds are germinated at a temperature that is non-permissive for seeds with the active temperature sensitivity gene. Because the seeds result from a sexual combination of gametes, even modifications of only one allele will become homozygous in the next generation and therefore expose the recessive phenotype. All plants that germinate at the elevated temperature are characterized as below for modifications at the other gene(s) targeted. This will provide non-transgenic plants carrying the targeted genome modification in a genetic background identical to the progenitor one. If necessary, the inactivated temperature sensitivity gene can be removed using a single backcross generation.

The invention also provides molecular assays for detecting and characterizing cells that have been modified by one or both of the genome editing proteins used in the methods of the invention. One of skill will recognize that a number of molecular assays can be used for this purpose. These assays include, for example, nucleic acid hybridization, PCR, sequencing, and the like. Methods using high throughput, non-destructive seed sampling for one or more markers, such as genetic markers are well known in the art. Apparatus and methods for the high throughput, non-destructive sampling of seeds have been described.

The methods of the invention can be used to introduce mutations into any desired target gene controlling any desired phenotype. The desired phenotype may be enhanced plant morphology, physiology, growth and development, color, shape, consumer preference, yield, nutritional enhancement, decreased accumulation of undesirable constituents such as heavy metals and secondary metabolites, disease or pest resistance, improved interactions with beneficial or deleterious microbes such as symbionts and microbiome constituents, or tolerance to abiotic stress. The phenotype may also be enhanced water use efficiency, enhanced cold tolerance, increased yield, enhanced nitrogen use efficiency, enhanced seed protein and enhanced seed oil, better post-harvest performance and less post-harvest losses. The desired phenotype may be enhanced yield including increased yield under non-stress conditions and increased yield under environmental stress conditions. Stress conditions may include, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability, anaerobic conditions, exposure to pollutants, and high plant density. Yield can be affected by many properties including for example, plant height, fruit or grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Yield can also be affected by efficiency of germination (including germination in stressed conditions), growth rate (including growth rate in stressed conditions), seed size, composition of seed (starch, oil, protein) and characteristics of seed fill.

One of skill will thus be able to choose an appropriate selection method based upon the desired phenotype. For example, where the desired phenotype is tolerance to a particular stress condition (e.g., drought, highly salinity, or anaerobic conditions) the methods of the invention include exposure of a population of plants to the stress conditions and selecting plants that show increased tolerance. Thus, a plant with the desired phenotype, when exposed to the stress condition, shows less of an effect, or no effect, in response to the condition as compared to a corresponding reference or control plant (naturally occurring wild-type plant or a plant not containing a mutation in the target gene).

EXAMPLES

The following examples are offered to illustrate, but not to limit the claimed invention.

Example 1

Development and Application of Whole Plant CRISPR Technology

The present invention provides a strategy of gene editing to introduce beneficial allelic variation that avoids going through tissue culture. This takes advantage of the temperature sensitivity of seed germination being determined by a single gene, LsNCED4 and the high rates of simultaneous genetic changes that occur with CRISPR-Cas9 technology. When CRISPR-mediated gene modifications occur, they often occur with high frequency, multiple times within the same cell. In some systems up to 60% of the cells contain homozygous changes, i.e. both alleles have been modified. If multiple genes are targeted simultaneously, up to 20% of cells have biallelic modifications in multiple genes and up to five genes have been modified simultaneously. If LsNCED4 is active, lettuce seed will not germinate above 30° C.; however, if this gene is knocked out, the seed will germinate well at temperatures above 30° C. Therefore, the ability to germinate at high temperature provides a powerful screen for inactivation of LsNCED4. All lettuce cultivars studied have an active LsNCED4 gene and therefore do not germinate at high temperatures. Consequently, this gene provides a natural selectable marker for gene modification that is present in most (possibly all) lettuce cultivars. Furthermore, inactivation of this gene seems to have no deleterious effect on the performance of the plant. Modification of meristematic cells in the shoot apex will provide non-transgenic plants carrying the targeted genome modification in a genetic background identical to the progenitor one.

To practice the invention, meristematic cells in the shoot apex of intact plants are modified using the CRISPR-Cas9 system. Multiple genes are targeted simultaneously. One is LsNCED4; during the testing of the system, the second gene is the UidA gene and the recipient plant will be transgenic expressing the UidA (GUS) gene, so that the frequency of single and double gene knockouts can be evaluated. Standard components are used, including the gene encoding Cas9 that has been codon optimized for expression in plants fused to the SV40 nuclear localization signal expressed from an apex-specific promoter such as that of the *Arabidopsis* INCURVATA2 gene Jiang, et al. (2103) *Nucl. Acids Res*. doi: 10.1093/nar/gkt780; Nekrasov, et at. (2103) *Nat. Biotechnol*. 31, 691-69. Shan, et at. (2013) *Nat. Biotechnol*. 31, 686-688; Xie, et at. (2013) *Molecular plant*. 6, 1975-1983). To avoid off-target cleavage CRISPR design tools that optimize the seed sequences are used; only seed sequences without any hits to the lettuce genome are used. A single guide RNA consisting of NGG 5' to 20 bases from the target gene plus PAM and tracrRNA sequences is expressed from the *Arabidopsis* U6 promoter so the RNA will be retained in the nucleus.

The constructs are tested using infiltration with *Agrobacterium* and microprojectile bombardment of the apices of ~month-old plants to provide transient gene expression in the shoot primordia. Plants are grown to maturity and allowed to self. The resultant seeds are germinated at 30° C. that is non-permissive for seeds with an active NCED4 gene. Because the seeds result from a combination of gametes, even modifications of only one allele will become homozygous in the next generation and therefore expose the recessive phenotype. Plants that germinate at the elevated temperature are selected and characterized for GUS expression as well as by PCR and sequencing to characterize the mutations occurring in the NCED4 and UidA genes. If no gene editing events are detected, the constructs are validated using conventional *Agrobacterium*-mediated transformation via tissue culture prior to attempts to optimize the shoot treatments.

Gene replacement protocols can be developed utilizing lines for which inactivated LsNCED4 has segregated away from the inactivated UidA gene. Constructs will again target LsNCED4; however the Cas9 plus guide RNA construct will be co-delivered with a functional UidA gene using TRV delivery (Baltes, et at. (2014) *Plant Cell.* 26:151-63).

Example 2

Genome Engineering to Generate Novel Chromosome Blocks so Combinations of Desired Traits can be Selected for as a Single Mendelian Unit The CRISPR-Cas9 system also provides the opportunity to generate multiple chromosome breaks in the genome and induce directed chromosome rearrangements (Lee, et at. (2012) *Genome Res.* 22, 539-548; Qi et al., (2013) G3. 3,1707-15). As an increasing number of chromosome regions are characterized as being advantageous it becomes increasingly difficult to generate and maintain ideal combinations of genes. One option is to generate a cassette of transgenes and generate a transgenic line; this, however, generates regulatory hurdles. Another option is to engineer the genome to place advantageous segments in proximal chromosomal positions so that they will be inherited as a single Mendelian unit with little recombination. This should have reduced regulatory hurdles compared to transgenic lines and will also allow manipulation of complex loci such as QTLs without complete molecular characterization.

Nucleases are designed to make double-strand breaks in the arms of two chromosomes to induce balanced translocations. Such translocations are expected, since similar simultaneous cleavages have been shown to induce up to 5 Mb deletions, duplications, and inversions. Loss of entire chromosomes can be induced by insertion of a thymidine kinase gene and appropriate selection pressure (Li et al., 2012 *Nat. Biotechnol.* 31, 688-691). We have similarly observed large deletions and inversions using CRISPR/Cas systems. To encourage translocation between non-homologous partners, polymorphisms are included in the target sites so that cleavage is favored on only one of the two homologs. Simultaneous cleavage of two non-homologous chromosomes will lead, in some portion of treated cells, to translocations by non-homologous end-joining repair. Such translocation can be identified by PCR amplification across the unique translocation junction, and validated by cytogenetic and FISH analysis. Further rounds of targeted translocation production are used to assemble the desired genomic regions in close physical proximity to segregate as single Mendelian units.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for selecting modified plants with a mutation in a target gene wherein the method does not use tissue culture, the method comprising a) introducing a first recombinant expression cassette encoding a first genome editing protein into meristematic or germline cells of a parent plant, wherein the first genome editing protein specifically recognizes the target gene;
b) introducing a second recombinant expression cassette encoding a second genome editing protein into meristematic or germline cells of the parent plant, wherein the second genome editing protein specifically recognizes a gene controlling seed germination, wherein the gene is LsNCED4;
c) after steps (a) and (b), crossing or selfing the parent plant, thereby producing a plurality of progeny seed;
d) selecting progeny plants grown from the progeny seed that are capable of germinating under heat conditions that inhibit germination of seed which lack a mutation in the gene controlling seed germination;
e) identifying the progeny plants selected in step (d) that comprise a mutation in the target gene, thereby selecting modified plants with a mutation in the target gene.

2. The method of claim 1, wherein the meristematic cells are in an apical meristem.

3. The method of claim 1, wherein the step of selecting progeny plants is carried out using first generation progeny.

4. The method of claim 1, wherein the first or second genome editing protein is a zinc finger nuclease.

5. The method of claim 1, wherein the first or second genome editing protein is a TALEN.

6. The method of claim 1, wherein the first or second genome editing protein is a Cas-9 nuclease guided by a guide RNA (gRNA).

7. The method of claims 1, wherein the first or second genome editing protein introduces a single strand nick or a double strand break in the target gene.

8. The method of claim 1, wherein the first genome editing protein is used to introduce a desired nucleotide sequence into the target gene by homologous recombination.

9. The method of claim 1, wherein the first or second recombinant expression cassette is introduced into the cells using Agrobacterium.

10. The method of claim 1, wherein the first or second recombinant expression cassette is introduced into the cells using particle bombardment.

11. The method of claim 1, wherein the first or second recombinant expression cassette is introduced into the cells using microinjection.

12. The method of claim 1, wherein the first or the second recombinant expression cassette is transiently expressed in the cells.

13. The method of claim 1, wherein the first and second expression cassettes are introduced into the plant in planta.

14. The method of claim 1, wherein the mutation in the target gene confers resistance to a plant pathogen.

15. The method of claim 1, wherein the mutation in the target gene confers resistance to stress conditions.

16. The method of claim 1, wherein the mutation in the target gene increases yield.

17. The method of claim 1, wherein the mutation in the target gene changes plant development, plant color, or sensitivity to a chemical.

* * * * *